US009848799B2

(12) United States Patent
Govari et al.

(10) Patent No.: US 9,848,799 B2
(45) Date of Patent: Dec. 26, 2017

(54) REAL-TIME GENERATION OF MRI SLICES

(71) Applicant: BIOSENSE WEBSTER (ISRAEL) LTD., Yokneam (IL)

(72) Inventors: Assaf Govari, Haifa (IL); Yitzhack Schwartz, Haifa (IL)

(73) Assignee: Biosense Webster (ISRAEL) Ltd, Yokneam (IL)

(*) Notice: Subject to any disclaimer, the term of this patent is extended or adjusted under 35 U.S.C. 154(b) by 801 days.

(21) Appl. No.: 14/314,128

(22) Filed: Jun. 25, 2014

(65) Prior Publication Data
US 2015/0374260 A1 Dec. 31, 2015

(51) Int. Cl.
G01V 3/00 (2006.01)
A61B 5/06 (2006.01)
A61B 5/055 (2006.01)
G01R 33/483 (2006.01)
A61B 5/00 (2006.01)
G01R 33/28 (2006.01)
G01R 33/48 (2006.01)
A61B 90/00 (2016.01)

(52) U.S. Cl.
CPC ............ *A61B 5/066* (2013.01); *A61B 5/0044* (2013.01); *A61B 5/055* (2013.01); *A61B 5/062* (2013.01); *A61B 5/6852* (2013.01); *A61B 5/748* (2013.01); *A61B 5/7425* (2013.01); *G01R 33/285* (2013.01); *G01R 33/48* (2013.01); *G01R 33/4833* (2013.01); *A61B 2090/374* (2016.02); *A61B 2576/023* (2013.01); *G01R 33/4822* (2013.01)

(58) Field of Classification Search
CPC ..................................................... A61B 5/055
USPC .................................................. 324/318, 322
See application file for complete search history.

(56) References Cited

U.S. PATENT DOCUMENTS

| 5,391,199 | A | 2/1995 | Ben-Haim |
|---|---|---|---|
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |
| 6,620,404 | B1 | 9/2003 | Quay |
| 6,675,034 | B2 | 1/2004 | Sussman |
| 6,690,963 | B2 | 2/2004 | Ben-Haim |
| 6,704,593 | B2 | 3/2004 | Stainsby |
| 6,898,302 | B1 | 5/2005 | Brummer |
| 6,968,225 | B2 | 11/2005 | Vu |
| 7,551,953 | B2 | 6/2009 | Lardo |
| 7,945,304 | B2 | 5/2011 | Feinberg |
| 7,953,469 | B2 | 5/2011 | Shankaranarayanan |
| 8,238,625 | B2 | 8/2012 | Strommer |

(Continued)

FOREIGN PATENT DOCUMENTS

| EP | 1421913 A1 | 5/2004 |
|---|---|---|
| EP | 2481350 A1 | 1/2012 |

(Continued)

*Primary Examiner* — Louis Arana
(74) *Attorney, Agent, or Firm* — Louis J. Capezzuto

(57) ABSTRACT

A method includes displaying a position of a distal end of a medical probe that is being navigated in an organ of a patient on a three-dimensional (3D) map of the organ. In response to an event, a plane of interest including the distal end is selected, a real-time Magnetic Resonance Imaging (MRI) slice of the organ is acquired at the selected plane, and the MRI slice is displayed overlaid on the 3D map.

8 Claims, 3 Drawing Sheets

(56) References Cited

U.S. PATENT DOCUMENTS

| | | | |
|---|---|---|---|
| 8,303,505 B2 * | 11/2012 | Webler | ............... G06F 19/3437 600/437 |
| 8,583,209 B2 | 11/2013 | Maier | |
| 8,620,404 B2 | 12/2013 | Mistretta | |
| 8,675,996 B2 | 3/2014 | Liao | |
| 8,676,300 B2 | 3/2014 | Strommer | |
| 8,805,034 B2 * | 8/2014 | Lehmann | ............... A61B 6/463 382/128 |
| 9,002,433 B2 * | 4/2015 | Aksit | ................... A61B 5/055 600/407 |
| 2002/0065455 A1 | 5/2002 | Ben-Haim | |
| 2003/0120150 A1 | 6/2003 | Govari | |
| 2004/0068178 A1 | 4/2004 | Govari | |
| 2006/0241465 A1 * | 10/2006 | Huennekens | ......... A61B 6/504 600/458 |
| 2010/0312094 A1 | 12/2010 | Guttman | |
| 2010/0317961 A1 | 12/2010 | Jenkins | |
| 2012/0053448 A1 * | 3/2012 | Griswold | ............... A61B 5/055 600/411 |
| 2013/0116543 A1 | 5/2013 | Jenkins | |
| 2013/0123598 A1 | 5/2013 | Jenkins | |
| 2013/0184569 A1 | 7/2013 | Strommer | |
| 2014/0043026 A1 | 2/2014 | Frahm | |

FOREIGN PATENT DOCUMENTS

| | | | |
|---|---|---|---|
| WO | WO 96-05768 A1 | 2/1996 | |
| WO | WO 2014/001974 A2 | 1/2014 | |

\* cited by examiner

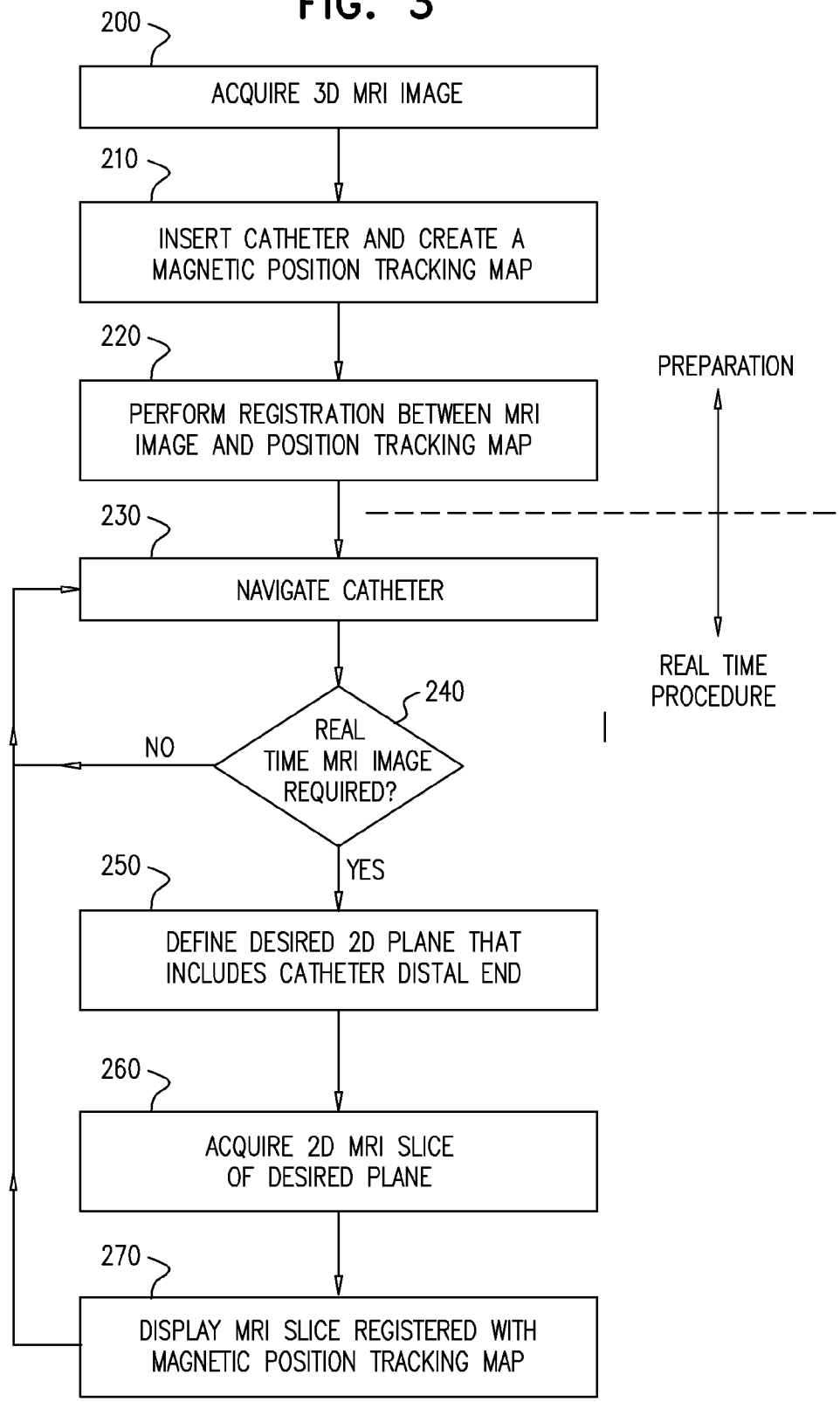

REAL-TIME GENERATION OF MRI SLICES

FIELD OF THE INVENTION

The present invention relates generally to medical imaging, and particularly to methods and systems for real-time MRI in interventional cardiology.

BACKGROUND OF THE INVENTION

Magnetic Resonance Imaging (MRI) is commonly used for medical imaging in a variety of applications. MRI processing is typically computationally intensive, and therefore real-time MRI for a large volume is usually feasible at relatively low spatial and temporal resolution.

U.S. Patent application publication 2010/0312094, to Guttman, et al., whose disclosure is incorporated herein by reference, describes MRI-guided surgical systems with preset scan planes. During ablation MR thermometry (2-D) can be used to show real-time ablation formation taking a slice along the catheter and showing the temperature profile increasing. It is contemplated that 2D and/or 3D GRE pulse sequences can be used to obtain the MR image data. However, other pulse sequences may also be used.

U.S. Pat. No. 8,620,404, to Mistretta, whose disclosure is incorporated herein by reference, describes system and method for generating time-resolved 3D medical images of a subject. The method includes acquiring a time series of two-dimensional (2D) data sets from a portion of the subject using a magnetic resonance imaging (MRI) system and reconstructing the time series of 2D data sets into a 2D time series of images of the subject having a given frame rate.

U.S. Patent application publication 2013/0184569, to Strommer, et al., whose disclosure is incorporated herein by reference, describes methods for producing an electrophysiological map of the heart. An example method may include determining a target location and an orientation of a catheter tip, confirming that the tip is located at the target location, measuring the heart parameter value at each of the target locations, and superimposing a plurality of representations of the heart parameter value.

U.S. Pat. No. 8,675,996, to Liao, et al., whose disclosure is incorporated herein by reference, describes a method for registering a two-dimensional image of a cardiocirculatory structure and a three-dimensional image of the cardiocirculatory structure. The method includes acquiring a three-dimensional image including the cardiocirculatory structure using a first imaging modality. The acquired three-dimensional image is projected into two-dimensions to produce a two-dimensional projection image of the cardiocirculatory structure. A structure of interest is segmented either from the three-dimensional image prior to projection or from the projection image subsequent to projection. A two-dimensional image of the cardiocirculatory structure is acquired using a second imaging modality.

U.S. Pat. No. 8,676,300, to Strommer, et al., whose disclosure is incorporated herein by reference, describes method and system for navigating through an occluded tubular organ. The procedures included injecting a first dye injection into the tubular organ, the first dye approaching a first end of the occluded segment. Multiple first-injection two-dimensional (2D) images of the tubular organ are acquired, each acquired from a different perspective, the first-injection 2D images further acquired with a respective organ timing signal reading.

SUMMARY OF THE INVENTION

An embodiment of the present invention that is described herein provides a medical system including an interface and a processor. The interface is configured to communicate with a Magnetic Resonance Imaging (MRI) system. The processor is configured to display a position of a distal end of a medical probe that is being navigated in an organ of a patient on a three-dimensional (3D) map of the organ, and, in response to an event, to select a plane of interest including the distal end, to acquire from the MRI system, via the interface, a real-time MRI slice of the organ at the selected plane, and to display the MRI slice overlaid on the 3D map.

In some embodiments, the 3D map of the organ is created by a 3D magnetic position tracking system. In other embodiments, the processor is configured to receive a selection of the plane from a user. In alternative embodiments, the processor is configured to choose the plane automatically in response to the event. In yet another embodiment, the organ includes a heart, and the medical probe includes a cardiac catheter.

There is additionally provided, in accordance with an embodiment of the present invention, a method including displaying a position of a distal end of a medical probe that is being navigated in an organ of a patient on a 3D map of the organ. In response to an event, a plane of interest including the distal end is selected, a real-time MRI slice of the organ is acquired at the selected plane, and the MRI slice is displayed overlaid on the 3D map.

The present invention will be more fully understood from the following detailed description of the embodiments thereof, taken together with the drawings in which:

BRIEF DESCRIPTION OF THE DRAWINGS

FIG. 3 is a flow chart which schematically illustrates a method for acquiring a real-time MRI image and overlaying it with a magnetic position tracking map during an intracardiac procedure, in accordance with an embodiment of the present invention.

DETAILED DESCRIPTION OF EMBODIMENTS

Overview

Some minimally invasive procedures use magnetic position tracking maps, such as provided by the Biosense Webster CARTO™ system, to navigate a catheter or other medical probe in a patient's body. In some events, a physician needs a real-time image of an organ near a catheter's distal end. MRI is one of the imaging solutions, but 3D MRI requires intensive calculations and therefore usually cannot provide the required resolution in real-time.

Embodiments of the present invention that are described herein below provide a method and system to obtain real-time imaging of the vicinity of the catheter's distal end during navigation, using a 3D magnetic position tracking map. Instead of acquiring a complete 3D MRI model, which is not feasible to perform in real time, the disclosed techniques acquire and display a MRI slice in a selected plane of interest which contains the catheter's distal end. By settling for an image at a specific plane, the physician can be provided with an overlaid image of an MRI slice on the magnetic position map in real-time.

In the context of the present patent application and in the claims, the terms "MRI slice" and "2D MRI slice" refer to a thin MRI slice (e.g., 3 millimeters in thickness) acquired by an MRI system on a specified 2D plane. For all practical purposes such a slice is regarded as two-dimensional, even though it has a finite thickness.

The embodiments described herein refer mainly to cardiac catheters and cardiac procedures. Alternative embodiments, however, are applicable for any minimally-invasive medical procedures such as laparoscopy or endoscopy, and are not limited to cardiac applications.

System Description

Figure 1:
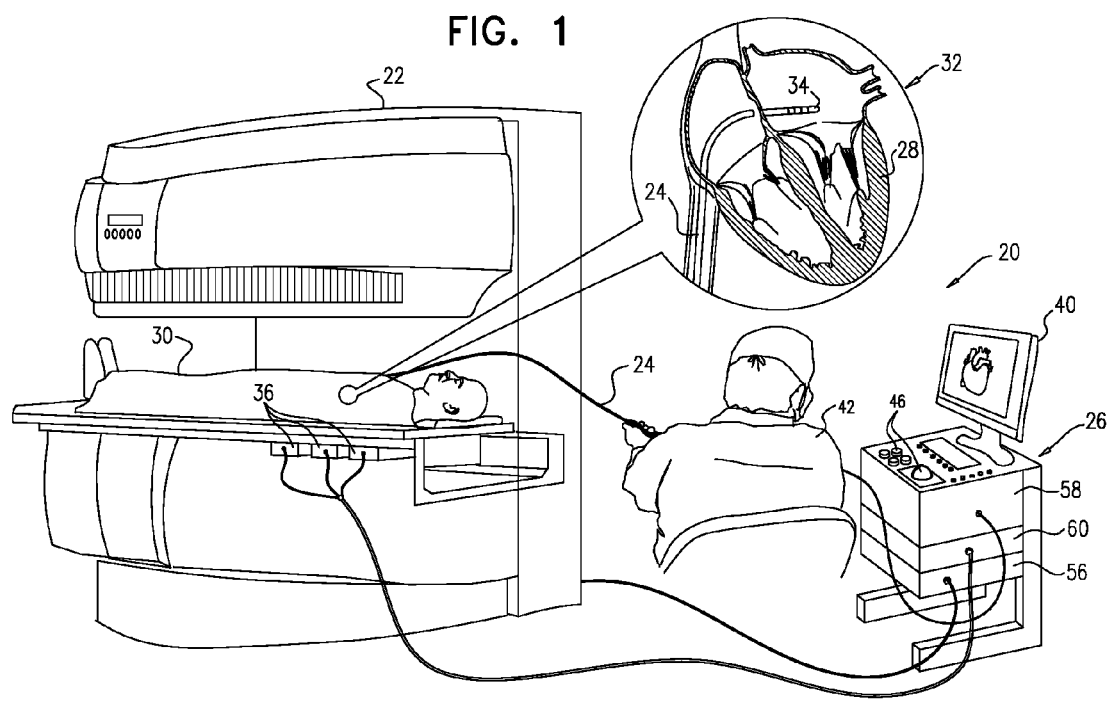
FIG. 1 is a schematic pictorial illustration of an MRI system and a magnetic position tracking system during a minimally invasive cardiac procedure, in accordance with an embodiment of the present invention.

FIG. 1 is a schematic pictorial illustration of an MRI system 22 and a magnetic position tracking system 20 during a minimally invasive cardiac procedure, in accordance with an embodiment of the present invention. MRI system 22 is connected to magnetic position tracking system 20 via an interface 56. Magnetic position tracking system 20 comprises a console 26, and a catheter 24, which comprises a distal end 34 as shown in an insert 32 of FIG. 1.

A cardiologist 42 navigates catheter 24 in a patient's heart 28, until distal end 34 reaches the desired location in this organ, and then cardiologist 42 performs the medical treatment using distal end 34. In other embodiments, the disclosed techniques can be used with procedures that are performed in any other organ, and instead of cardiologist 42, any suitable human user can use the system.

This method of position tracking is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Console 26 comprises a processor 58, a driver circuit 60, interface 56 to MRI system 22, input devices 46, and a display 40. Driver circuit 60 drives magnetic field generators 36, which are placed at known positions below a patient's 30 torso. In response to an event, cardiologist 42 selects (using input devices 46 and a suitable Graphical User Interface (GUI) on screen 40) a desired plane, which comprises distal end 34. In another embodiment, processor 58 selects the desired plane automatically. Processor 58 requests a MRI slice of the selected plane from MRI system 22, via interface 56. MRI system 22 acquires the requested slice and sends it, via interface 56, to processor 58.

Processor 58 creates an overlaid image of a 3D magnetic position tracking map with a MRI slice and displays this image on screen 40.

The configuration of system 20 shown in FIG. 1 is an example configuration, which is chosen purely for the sake of conceptual clarity. In alternative embodiments, any other suitable configuration can be used for implementing the system. Certain elements of system 20 can be implemented using hardware, such as using one or more Application-Specific Integrated Circuits (ASICs) or Field-Programmable Gate Arrays (FPGAs) or other device types. Additionally or alternatively, certain elements of system 20 can be implemented using software, or using a combination of hardware and software elements.

Processor 58 typically comprises a general-purpose computer, which is programmed in software to carry out the functions described herein. The software may be downloaded to the computer in an electronic form, over a network, for example, or it may, alternatively or additionally, be provided and/or stored on non-transitory tangible media, such as magnetic, optical, or electronic memory.

Real-Time Overlay of a MRI Slice on 3D Map

Minimally-invasive procedures require external imaging since the physician cannot see the probe during its navigation and treatment. In embodiments of the present invention processor 58 uses the magnetic position tracking capability of system 20 to produce and display a 3D map of the patient heart, overlaid with an image of distal end 34, so cardiologist 42 knows the exact location and orientation of distal end 34 with respect to heart 28.

During the navigation and treatment process, cardiologist 42 may need images of the pertinent organ around distal end 42, in real time. In case of MRI, acquisition of a full volume 3D MRI image takes a long time as it requires volumetric scanning and intensive calculations. Other imaging techniques, such as X-RAY fluoroscopy, may acquire an image faster than 3D MRI, but there are cases where MRI is needed for the particular treatment and in order to minimize undesired radiation. The embodiments described herein fulfill the need for real-time MRI during minimally-invasive procedures in cardiology, and is also suitable for other minimally-invasive medical procedures.

In case an MRI image is needed in the vicinity of the catheter's distal end, cardiologist 42 selects a pertinent plane within patient's heart 28, which includes distal end 34. Cardiologist 42 defines the desired plane by using input devices 46 and a suitable GUI on screen 40, and processor 58 converts the selected plane into a request for MRI system 22. In response to such an event, processor 58 sends a request to MRI system 22, via interface 56, to acquire a MRI slice of the desired plane, which comprises distal end 34.

Since a MRI slice covers a relatively small area and does not require intensive calculations, it can be acquired in real-time. MRI system 22 acquires the requested slice and sends it back to processor 58 via interface 56. Processor 58 creates an overlaid image of the 3D magnetic position tracking map with the recently-acquired MRI slice and displays it on screen 40. The overlaid image provides cardiologist 42 a real-time, up-to-date, high-resolution view of the tissue in the vicinity of distal end 34, for the navigation and therapeutic ablation procedures. In an alternative embodiment processor 58 selects the desired plane automatically, e.g., in response to a specific event, or periodically.

Figure 2:
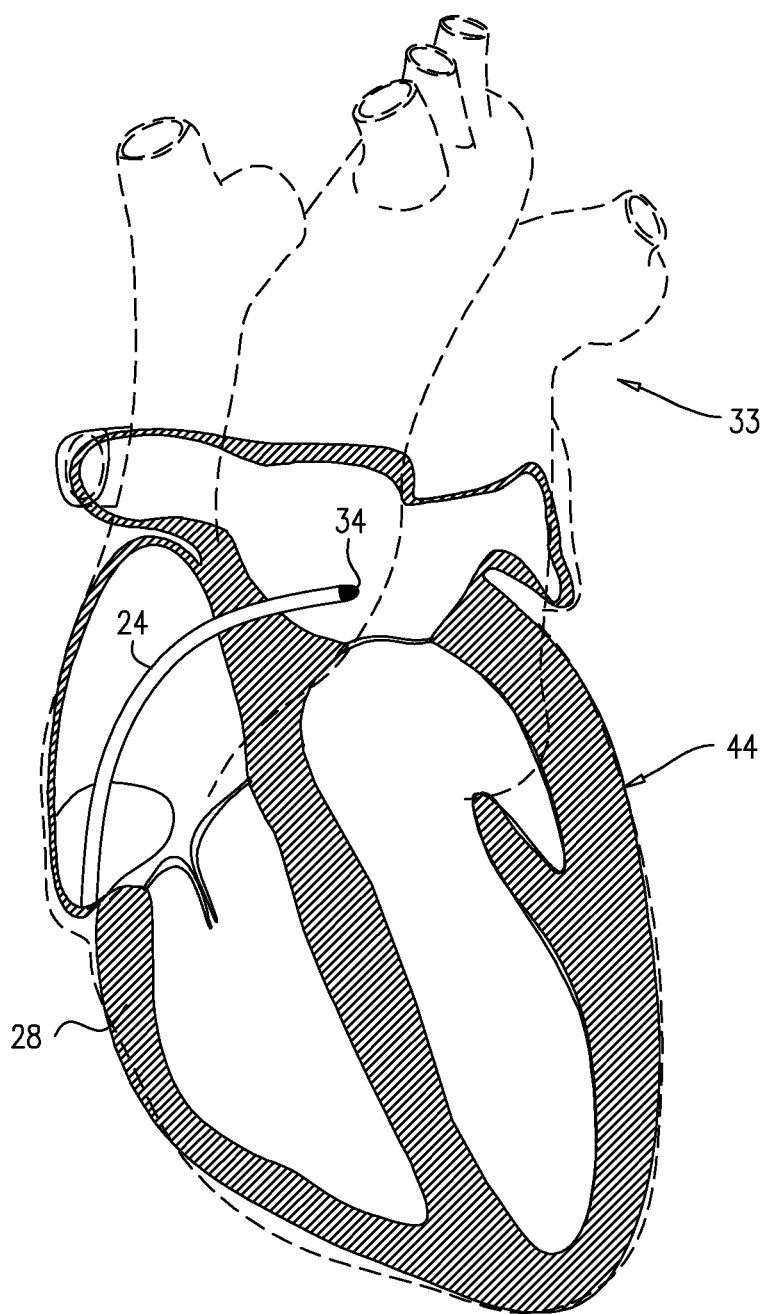
FIG. 2 is a schematic pictorial illustration of a MRI slice overlaid on a three-dimensional (3D) magnetic position tracking map, in accordance with an embodiment of the present invention.

FIG. 2 is a schematic pictorial illustration of a MRI slice overlaid on a 3D magnetic position tracking map, in accordance with an embodiment of the present invention. MRI system 22 and magnetic position tracking systems 20 generate a MRI slice 44 and a position tracking map 33, respectively. To produce this overlaid image, as described above, cardiologist 42 selects a plane of interest comprising distal end 34 in patient's heart 28, and processor 58 commands MRI system 22, via interface 56, to acquire a MRI slice 44. MRI system 22 creates MRI slice 44 and sends it to processor 58 via interface 56. Processor 58 displays the overlaid image of slice 44 on 3D position tracking map 33 on screen 40.

The overlaid image provides cardiologist 42 a real-time high-resolution input for the navigation and treatment procedures. In an alternative embodiment processor 58 selects the desired plane automatically.

FIG. 3 is a flow chart that schematically illustrates a method for acquiring a real-time MRI image and overlaying it with a magnetic position tracking map during an intra-cardiac procedure, in accordance with an embodiment of the present invention. In this example, the method is divided into a preparation stage and a real-time procedure stage. In other embodiments, however, the method can comprise the real-time procedure stage without the preparation stage as, once the MRI scanner and CARTO system are installed and co-registered, the inserted catheter is inherently already registered with the MRI frame of reference.

The method begins at a 3D MRI acquisition step 200, when the MRI system acquires a 3D image in patient's heart 28. At a catheter insertion step 210, cardiologist 42 inserts catheter 24 to the patient's heart and magnetic position tracking system 20 creates a magnetic position tracking map in the area of the distal end location. At a registration step 220, the system performs registration to create an overlaid image between the 3D MRI image, which was acquired at 3D MRI acquisition step 200, and the 3D magnetic position tracking map, which was acquired at catheter insertion step 210. This overlaid image helps cardiologist 42 to plan the medical procedure and to navigate distal end 34 to the target locations in patient's heart 28.

At a navigation step 230, cardiologist 42 navigates catheter 24 to the target location in the patient's heart using the 3D position tracking map and the 3D MRI image. During the navigation, cardiologist 42 may need an updated local MRI image near the distal end of catheter 24. At a decision step 240, cardiologist 42 decides to acquire an MRI image for improved navigation or treatment reasons.

The need for additional real-time images may be a result of unexpected events during the procedure, such as obstacles encountered during catheter 24 navigation, or to verify that a specific treatment is performed in the target location. Further alternatively, any other suitable event may warrant an acquisition of a MRI slice.

If a slice is not needed, the method loops back to navigation step 230 above, in which cardiologist 42 continues to navigate catheter 24. If decision step 240 concludes that a MRI slice is needed, then the method proceeds to a plane definition step 250. At plane definition step 250, cardiologist 42 examines the pertinent organ on display 40, and uses input devices 46 and a suitable GUI on display 40 to select the desired plane, which comprises catheter's distal end 34.

At a slice acquisition step 260, processor 58 sends a request to MRI system 22, via interface 56, to acquire a MRI slice of the plane selected at plane definition step 250 above. The request specifies the pertinent plane to MRI system 22, using any suitable convention (e.g. plane equations in some common coordinate system). In some embodiments processor 58 also indicates the position coordinates of distal end 34 to MRI system 22. In response to the request, MRI system 22 acquires the requested MRI slice and sends it to processor 58 via interface 56.

Processor 58 receives MRI slice 44 and performs registration between MRI slice 44 and 3D magnetic position tracking map 33. At a display step 270, processor 58 displays the overlaid image between MRI slice 44 and 3D magnetic position tracking map 33 on display 40.

If applicable, cardiologist 42 continues navigation or treatment, as described in navigation step 230 and can request additional real-time MRI images for the same plane, as described in plane definition step 250, or for other planes in the vicinity of distal end 34.

FIG. 3 shows a specific flow of operations; however the techniques described herein are not limited to this specific flow. In other embodiments the flow may exclude the preparation stage (steps 200, 210, and 220) and start, for example, directly with the real-time stage (at step 230). In another embodiment the plane selection can be done automatically by the system, in specific events or on a periodic basis.

The disclosed techniques can be used in various applications, such as the following six examples:

(1) Acquiring a thin slice of the inter-atrial septum (fossa ovalis) for safely performing a transseptal procedure (crossing the inter-atrial septum from the right atrium to the left atrium).

(2) Acquiring a thin slice of the Pulmonary Vein os for preplanning and execution of a Pulmonary Vein Isolation procedure.

(3) Acquiring a thin slice of an Atrio-Ventricular (Tricuspid or Mitral Valves) or Ventriculo-Atrial Valve (Pulmonary or Aortic Valve) for safe crossing, planning and performing of catheter-based repair or replacement of a cardiac valve.

(4) Acquiring a thin slice of the posterior Left Atrium for depiction of the Esophagus, its course and distance from a planned ablation point or line. Re-acquiring the same slice after completing the ablation procedure to rule out immediate post ablation Esophageal damages (edema, ulceration, perforation).

(5) Acquiring a thin slice to depict the Right Phrenic Nerve and distance of the nerve from a planned ablation point or line.

(6) Acquiring a sequence of thin slices to monitor and assess lesion formation all through an ablation.

Although the embodiments described herein mainly address cardiology, the methods and systems described herein can also be used in other minimally invasive applications, such as endoscopy and laparoscopy.

Although the embodiments described herein mainly address therapeutic cardiac ablation procedures like treatment of Atrial-Fibrillation, the methods and systems described herein can also be used in other applications. For example, the methods and/or systems can be used for guided needle biopsies, deployment of hepato-billiary stents, exclusion of Abdominal Aortic Aneurysm via stent, and modulation of the Autonomic Nervous System via ablation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
    displaying a position of a distal end of a medical probe that is being navigated in an organ of a patient on a three-dimensional (3D) map of the organ; and
    in response to an event, selecting a plane of interest comprising the distal end, acquiring a real-time Magnetic Resonance Imaging (MRI) slice of the organ at the selected plane, and displaying the MRI slice overlaid on the 3D map;

wherein the 3D map of the organ is created by a 3D magnetic position tracking system.

2. The method according to claim 1, wherein selecting the plane of interest comprises receiving a selection of the plane from a user.

3. The method according to claim 1, wherein selecting the plane of interest comprises choosing the plane automatically in response to the event.

4. The method according to claim 1, wherein the organ comprises a heart, and wherein the medical probe comprises a cardiac catheter.

5. A system, comprising:
an interface, which is configured to communicate with a Magnetic Resonance Imaging (MRI) system; and
a processor, which is configured to display a position of a distal end of a medical probe that is being navigated in an organ of a patient on a three-dimensional (3D) map of the organ, and, in response to an event, to select a plane of interest comprising the distal end, to acquire from the MRI system, via the interface, a real-time MRI slice of the organ at the selected plane, and to display the MRI slice overlaid on the 3D map;

wherein the 3D map of the organ is created by a 3D magnetic position tracking system.

6. The system according to claim 5, wherein the processor is configured to receive a selection of the plane from a user.

7. The system according to claim 5, wherein the processor is configured to choose the plane automatically in response to the event.

8. The system according to claim 5, wherein the organ comprises a heart, and wherein the medical probe comprises a cardiac catheter.

\* \* \* \* \*